US012778045B2

(12) United States Patent
Gifford et al.

(10) Patent No.: US 12,778,045 B2
(45) Date of Patent: Nov. 3, 2026

(54) SORGHUM HYBRID R20T2013

(71) Applicant: PIONEER HI-BRED INTERNATIONAL, INC., Johnston, IA (US)

(72) Inventors: Justin M. Gifford, Lubbock, TX (US); Maria Laura Mayor, Manhattan, KS (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 67 days.

(21) Appl. No.: 18/952,050

(22) Filed: Nov. 19, 2024

(65) Prior Publication Data

US 2026/0137053 A1 May 21, 2026

(51) Int. Cl.
*A01H 6/46* (2018.01)
*A01H 5/10* (2018.01)

(52) U.S. Cl.
CPC ............. *A01H 6/4666* (2018.05); *A01H 5/10* (2013.01)

(58) Field of Classification Search
None
See application file for complete search history.

(56) References Cited

U.S. PATENT DOCUMENTS 8,362,330 B2 * 1/2013 Johnson ............... A01H 6/4666 800/278
12,342,777 B1 7/2025 Mayor

OTHER PUBLICATIONS

U.S. Appl. No. 18/804,503 for Sorghum Hybrid XS8479, filed Dec. 13, 2021.
U.S. Appl. No. 18/952,001 for Sorghum Inbred 2PWJK39R, filed Nov. 19, 2024.

* cited by examiner

*Primary Examiner* — Mykola V. Kovalenko

(57) ABSTRACT

A novel sorghum variety designated R20T2013 and seed, plants, plant parts and plant cells thereof are produced from a cross of inbred sorghum varieties. Methods for producing a sorghum plant comprise crossing hybrid sorghum variety R20T2013 with another sorghum plant. Sorghum variety R20T2013, the seed, the plant produced from the seed, and variants, mutants, and minor modifications of sorghum variety R20T2013 are provided. Methods for producing a sorghum plant containing in its genetic material one or more traits introgressed into sorghum variety R20T2013 include one or both of backcross conversion and transformation of one or both inbred parents. The sorghum seed, plants and plant parts produced thereby are described.

20 Claims, No Drawings

SORGHUM HYBRID R20T2013

BACKGROUND

One goal of plant breeding is to combine, in a single hybrid, various desirable traits. For field crops, these traits may include resistance to diseases and insects, resistance to heat and drought, reducing the time to crop maturity, greater yield, and better agronomic quality. Uniformity of plant characteristics such as germination and stand establishment, growth rate, maturity, plant height and fruit size facilitate mechanical harvesting. Traditional plant breeding through the development and use of inbred varieties facilitates the development of new and improved commercial crops.

SUMMARY

Provided a novel sorghum, *Sorghum bicolor* (L.) Moench, variety, seed, plant, and its parts designated as R20T2013, produced by crossing two Pioneer Hi-Bred International, Inc. proprietary sorghum inbred varieties. Discloses are the hybrid sorghum variety R20T2013 the seed, the plant and its parts produced from the seed, and variants, mutants and minor modifications of sorghum R20T2013. Processes for making a sorghum plant containing in its genetic material one or more traits introgressed into R20T2013 through locus conversion and/or transformation, and to the sorghum seed, plant and plant parts produced thereby are also provided. Further disclosed are methods for producing sorghum varieties derived from hybrid sorghum variety R20T2013.

Definitions

In the description and examples that follow, a number of terms are used herein. In order to provide a clear and consistent understanding of the specification and claims, including the scope to be given such terms, the following definitions are provided:

Anthracnose Resistance. This is a visual rating based on the number of lesions caused by anthracnose infection. A score of 9 would indicate little necrosis and a score of 1 would indicate plant death as a result of anthracnose infection.

Bacterial Spot. Bacterial Spot is a disease characterized by small, irregularly shaped lesions on the leaves. Bacterial Spot Resistance is rated on a scale of 1 to 9, with 1 being susceptible and 9 being resistant.

Bacterial Streak. Bacterial Streak is a disease characterized by narrow yellow stripes on the leaves. Bacterial Streak Resistance is rated on a scale of 1 to 9, with 1 being susceptible and 9 being resistant.

Bacterial Stripe. Bacterial Stripe is a disease characterized by long, narrow red stripes on the leaves. Bacterial Stripe Resistance is rated on a scale of 1 to 9, with 1 being susceptible and 9 being resistant.

Biotype C Greenbug Resistance. This is a visual rating based on the amount of necrosis on leaves and stems caused by biotype C greenbug feeding. A score of 9 would indicate no leaf or stem damage as a result of greenbug feeding.

Biotype E Greenbug Resistance. This is a visual rating based on plant seedlings ability to continue growing when infested with large numbers of biotype E greenbugs. A score of 9 indicates normal growth and a score of 1 indicates seedling death.

Charcoal Rot. Charcoal Rot is a disease characterized by rotting of the roots and stalks. Charcoal Rot Resistance is rated on a scale of 1 to 9, with 1 being susceptible and 9 being resistant.

Chinch Bug Resistance. This is a visual rating based on the plants ability to grow normally when infested with large numbers of chinch bugs. A score of 9 would indicate normal growth and a score of 1 would indicate severe plant stunting and death.

Crop Response to Herbicide. Rated as the visual difference between sprayed and un-sprayed plants. A crop response of less than 30% means no visual difference, higher percentages means sprayed plants showed some damage.

Days to Flower. The days to flower is the number of days required for an inbred line or hybrid to shed pollen from the time of planting.

Days to Color. The days to color is the number of days required for an inbred line or hybrid to begin grain coloring from the time of planting. Coloring of the grain is correlated with physiological maturity, thus days to color gives an estimate of the period required before a hybrid is ready for harvest.

Days to Flower. The days to flower is the number of days required for an inbred line or hybrid to shed pollen from the time of planting.

Downy Mildew Resistance (Pathotypes 1 and 3). This is a visual rating based on the percentage of downy mildew infected plants. A score of 9 indicates no infected plants. A score of 1 would indicate higher than 50% infected plants. Ratings are made for infection by each pathotype of the disease.

Drought Tolerance. This represents a rating for drought tolerance and is based on data obtained under stress. It is based on such factors as yield, plant health, lodging resistance and stay green. A high score would indicate a hybrid tolerant to drought stress.

Dry Down. This represents the relative rate at which a hybrid will reach acceptable harvest moisture compared to other hybrids. A high score indicates a hybrid that dries relatively fast while a low score indicates a hybrid that dries slowly.

*Fusarium* Root and Stalk Rot. *Fusarium* Root and Stalk Rot is a disease characterized by rotting of the roots and stalks. *Fusarium* Root and Stalk Rot Resistance is rated on a scale of 1 to 9, with 1 being susceptible and 9 being resistant.

Grain Mold. Grain Mold is characterized by the formation of mold on heads and grain. Grain Mold Resistance is rated on a scale of 1 to 9, with 1 being susceptible and 9 being resistant.

Gray Leaf Spot Resistance. This is a visual rating based on the number of gray leaf spot lesions present on the leaves and stem of the sorghum plant. A score of 9 would indicate the presence of few lesions.

Head Exertion. This represents a rating for the length of the peduncle exposed between the base of the panicle (head) and the flag leaf of the plant. A high score indicates more distance between the flag leaf and the sorghum head while a low score indicates a short distance between the two. Head exertion facilitates ease of combine harvesting.

Head Smut Resistance (Races 1-4). This is a visual rating based on the percentage of smut infected plants. A score of 9 would indicate no infected plants and a score of 1 would indicate higher than 50% infected plants. Ratings are made for each race of head smut Head Type. This represents a rating of the morphology of the sorghum panicle (head). A high score indicates an open panicle caused by either more distance between panicle branches or longer panicle branches. A low score indicates a more compact panicle caused by shorter panicle branches arranged more closely on the central rachis.

Leaf Burn Resistance. This is a visual rating based on the amount of tissue damage caused by exposure to insecticide sprays. A score of 9 would indicate minor leaf spotting and a score of 1 would indicate leaf death as a result of contact with insecticide spray.

Locus Conversion (Also called a Trait Conversion): A locus conversion of a hybrid refers to hybrid plants that have inbred parents developed by backcrossing or genetic transformation to introduce a trait, wherein the morphological and physiological characteristics of the inbred are recovered in addition to the characteristics conferred by the locus transferred into the inbred via the backcrossing or genetic transformation. Traits can be directed to, for example, modified grain, modified carbohydrate content, modified oil content, male sterility, insect control, disease control or herbicide tolerance. Traits that can be introduced include one or more of mutant genes, transgenic sequences, genome edited sequences or allelic variants of native traits. A single locus conversion refers to plants that have been modified in a manner that retains the overall genetics of the variety and include a single locus with one or more specific desired traits. A single locus conversion can include a molecular stack of at least or about 1, 2, 3, 4 or 5 traits and less than or about 10, 9, 8, 7 or 6 traits, genes or modifications. A locus converted plant can include, for example, at least or about 1, 2 or 3 and less than or about 10, 9, 8, 7, 6, or 5 modified loci while still retaining the overall genetics of the variety and otherwise having essentially the same, the same, all or essentially all of the physiological and morphological characteristics of the variety, such as listed in Table 1. The total number of traits at one or more locus conversions can be, for example, at least or about 1, 2, 3, 4 or 5 and/or less than or about 20, 15, 10, 9, 8, 7 or 6. Examples of single locus conversions include mutant genes, transgenes and native traits finely mapped to a single locus. Traits may be introduced by transformation, backcrossing, or a combination of both.

Maize Dwarf Mosaic Virus Resistance. This is a visual rating based on the percentage of sorghum plants showing symptoms of virus infection. A score of 9 would indicate no plants with virus symptoms and a 1 would indicate a high percentage of plants showing symptoms of virus infection such as stunting, red leaf symptoms or leaf mottling.

Midge Resistance. This is a visual rating based on the percentage of seed set in the panicle in the presence of large numbers of midge adults. A score of 9 would indicate near normal seed set and a score of 1 would indicate no seed set in the head due to midge damage.

Moisture. The moisture is the actual percentage moisture of the grain at harvest.

Plant: As used herein, the term “plant” includes reference to an immature or mature whole plant, including a plant from which seed or grain has been removed.

Plant Height. This is a measure of the average height of the hybrid from the ground to the tip of the panicle and is measured in inches.

Plant Part: As used herein, the term “plant part” includes leaves, stems, roots, seed, grain, kernels, panicles, embryo, pollen, ovules, flowers, stalks, root tips, anthers, pericarp, protoplasts, tissue, plant calli, cells and the like. In some embodiments the plant part contains at least one cell of hybrid sorghum variety R20T2013.

Percent Yield. The percent yield is the yield obtained from the hybrid in terms of percent of the mean for the experiment in which it was grown.

Predicted RM. This trait, predicted relative maturity (RM), for a hybrid is based on the number of days required for an inbred line or hybrid to shed pollen from the time of planting. The relative maturity rating is based on a known set of checks and utilizes standard linear regression analyses.

*Puccinia* (Rust) Resistance. This is a visual rating based on the number of rust pustules present on the leaves and stem of the plant. A score of 9 would indicate the presence of few rust pustules.

RM to Color. This trait for a hybrid is based on the number of days required for a hybrid to begin to show color development in the grain from the time of planting. The relative maturity rating is based on a known set of checks and utilizes standard linear regression analyses.

Root Lodging. This represents a rating of the percentage of plants that do not root lodge, i.e. those that lean from the vertical axis at an approximate 30 degree angle or greater without stalk breakage are considered to be root lodged. This is a relative rating of a hybrid to other hybrids for standability. Root lodging is rated on a scale of 1 to 9, with 1 indicating greater than 50% lodged plants and 9 indicating no lodged plants.

Sales Appearance. This represents a rating of the acceptability of the hybrid in the market place. It is a complex score including such factors as hybrid uniformity, appearance of yield, grain texture, grain color and general plant health. A high score indicates the hybrid would be readily accepted based on appearance only. A low score indicates hybrid acceptability to be marginal based on appearance only.

Salt Tolerance. This represents a rating of the plants ability to grow normally in soils having high sodium salt content. This is a relative rating of a hybrid to other hybrids for normal growth.

Selection Index. The selection index gives a single measure of the hybrid’s worth based on information for up to five traits. A sorghum breeder may utilize his or her own set of traits for the selection index. Two of the traits that are almost always included are yield and days to flower (maturity). The selection index data presented in the tables in the specification represent the mean values averaged across testing stations.

Stalk Lodging. This represents a rating of the percentage of plants that do not stalk lodge, i.e. stalk breakage above the ground caused by natural causes. This is a relative rating of a hybrid to other hybrids for standability. Stalk lodging is rated on a scale of 1 to 9, with 1 indicating greater than 50% lodged plants and 9 indicating no lodged plants.

Stay Green. Stay green is the measure of plant health near the time of harvest. A high score indicates better late-season plant health.

Test Weight. This is the measure of the weight of the grain in pounds for a given volume (bushel) adjusted for percent moisture.

Weathering. This represents a rating of how well the exposed grains are able to retain normal seed quality when exposed to normal weather hazards and surface grain molds.

Yield (cwt/acre). The yield in cwt/acre is the actual yield of the grain at harvest adjusted to 13% moisture.

Yield/RM. This represents a rating of a hybrid yield compared to other hybrids of similar maturity or RM. A high score would indicate a hybrid with higher yield than other hybrids of the same maturity.

Yield Under Stress. This is a rating of the plants ability to produce grain under heat and drought stress conditions. A score of 9 would indicate near normal growth and grain yield and a score of 1 would indicate substantial yield reduction due to stress.

Zonate Leaf Spot Resistance. This is a visual rating based on the number of zonate leaf spot lesions present on the leaves and stem of the sorghum plant. A score of 9 would indicate the presence of few lesions.

DETAILED DESCRIPTION

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants that are each heterozygous at a number of gene loci will produce a population of hybrid plants that differ genetically and will not be uniform.

Sorghum plants (*Sorghum bicolor* L. Moench) are bred in most cases by self-pollination techniques. With the incorporation of male sterility (either genetic or cytoplasmic) cross pollination breeding techniques can also be utilized. Sorghum has a perfect flower with both male and female parts in the same flower located in the panicle. The flowers are usually in pairs on the panicle branches. Natural pollination occurs in sorghum when anthers (male flowers) open and pollen falls onto receptive stigma (female flowers). Because of the close proximity of male (anthers) and female (stigma) in the panicle, self-pollination is very high (average 94%). Cross pollination may occur when wind or convection currents move pollen from the anthers of one plant to receptive stigma on another plant. Cross pollination is greatly enhanced with incorporation of male sterility which renders male flowers nonviable without affecting the female flowers. Successful pollination in the case of male sterile flowers requires cross pollination.

Sorghum is in the same family as maize and has a similar growth habit, but with more tillers and a more extensively branched root system. Sorghum is more drought resistant and heat-tolerant than maize. It requires an average temperature of at least 25° C. to produce maximum yields. Sorghum's ability to thrive with less water than maize may be due to its ability to hold water in its foliage better than maize. Sorghum has a waxy coating on its leaves and stems which helps to keep water in the plant even in intense heat. Wild species of sorghum tend to grow to a height of 1.5 to 2 meters; however in order to improve harvestability, dwarfing genes have been selected in cultivated varieties and hybrids such that most cultivated varieties and hybrids grow to between 60 and 120 cm tall.

Hybrid Development

The development of sorghum hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$, $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

Sorghum varieties are mainly self-pollinated; therefore, self-pollination of the parental varieties must be controlled to make hybrid development feasible. A pollination control system and effective transfer of pollen from one parent to the other offers improved plant breeding and an effective method for producing hybrid seed and plants. For example, the milo or $A_1$ cytoplasmic male sterility (CMS) system, developed via a cross between milo and kafir cultivars, is one of the most frequently used CMS systems in hybrid sorghum production (Stephens J C & Holland P F, *Cytoplasmic Male Sterility for Hybrid Sorghum Seed Production*, Agron. J. 46:20-23 (1954)). Other CMS systems for sorghum include, but are not limited to, $A_2$, isolated from IS 12662c (Schertz K F, *Registration of* $A_2T_x$ 2753 *and* $BT_x$ 2753 *Sorghum Germplasm*, Crop Sci. 17: 983 (1977)), $A_3$, isolated from IS 1112c or converted Nilwa (Quinby J R, *Interactions of Genes and Cytoplasms in Male-Sterility in Sorghums*, Proc. 35th Corn Sorghum Res. Conf. Am. Seed Trade Assoc. Chicago, Ill., pp. 5-8 (1980)), $A_4$, isolated from IS 7920c (Worstell et al, *Relationship among Male-Sterility Inducing Cytoplasms of Sorghum*, Crop Sci. 24:186-189 (1984)).

In developing improved new sorghum hybrid varieties, breeders may use a CMS plant as the female parent. In using these plants, breeders attempt to improve the efficiency of seed production and the quality of the $F_1$ hybrids and to reduce the breeding costs. When hybridization is conducted without using CMS plants, it is more difficult to obtain and isolate the desired traits in the progeny ($F_1$ generation) because the parents are capable of undergoing both cross-pollination and self-pollination. If one of the parents is a CMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS female parent with a pollen-producing male parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self-pollination of the $F_1$ generation to produce several subsequent generations ensures that a desired trait is heritable and stable and that a new variety has been isolated.

Promising advanced breeding lines commonly are tested and compared to appropriate standards in environments representative of the commercial target area(s). The best lines are candidates for new commercial lines; and those still deficient in a few traits may be used as parents to produce new populations for further selection.

A hybrid sorghum variety is the cross of two inbred lines. The hybrid progeny of the first generation is designated $F_1$. In the development of hybrids only the F1 hybrid plants are sought. The F1 hybrid is more vigorous than its inbred parents. This hybrid vigor, or heterosis, can be manifested in many ways, including increased vegetative growth and increased yield.

The development of a hybrid sorghum variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny ($F_1$).

Because sorghum is normally a self-pollinated plant and because both male and female flowers are in the same panicle, large numbers of hybrid seed can only be produced by using cytoplasmic male sterile (CMS) inbreds. Flowers of the CMS inbred are fertilized with pollen from a male fertile inbred carrying genes which restore male fertility in the hybrid ($F_1$) plants. Once the inbreds that produce the best hybrid have been identified, the hybrid seed can be reproduced indefinitely as long as the homogeneity of the inbred parents is maintained.

A single cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not used for planting stock.

Hybrid sorghum can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign sorghum pollen, the stigma of the male sterile inbred (female) will be fertilized only with pollen from the male fertile inbred (male). The resulting seed, born on the male sterile (female) plants is therefore hybrid and will form hybrid plants that have full fertility restored.

Genotypic Characteristics of Variety R20T2013

In addition to phenotypic observations, a plant can also be described or identified by its genotype. The genotype of a plant can be characterized through a genetic marker profile. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Particular markers used for these purposes may include any type of marker and marker profile which provides a means of distinguishing varieties. A genetic marker profile can be used, for example, to identify plants of the same variety or related varieties or to determine or validate a pedigree. In addition to being used for identification of sorghum variety R20T2013, its inbred parents, and its plant parts, the genetic marker profile is also useful in developing a locus conversion of R20T2013.

Methods of isolating nucleic acids from sorghum plants and methods for performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

A method comprising isolating nucleic acids, such as DNA, from a plant, a plant part, plant cell or a seed of the sorghum plants disclosed herein is provided. The method can include mechanical, electrical and/or chemical disruption of the plant, plant part, plant cell or seed, contacting the disrupted plant, plant part, plant cell or seed with a buffer or solvent, to produce a solution or suspension comprising nucleic acids, optionally contacting the nucleic acids with a precipitating agent to precipitate the nucleic acids, optionally extracting the nucleic acids, and optionally separating the nucleic acids such as by centrifugation or by binding to beads or a column, with subsequent elution, or a combination thereof. If DNA is being isolated, an RNase can be included in one or more of the method steps. The nucleic acids isolated can comprise all or substantially all of the genomic DNA sequence, all or substantially all of the chromosomal DNA sequence or all or substantially all of the coding sequences (cDNA) of the plant, plant part, or plant cell from which they were isolated. The amount and type of nucleic acids isolated may be sufficient to permit whole genome sequencing of the plant from which they were isolated or chromosomal marker analysis of the plant from which they were isolated.

The methods can be used to produce nucleic acids from the plant, plant part, seed or cell, which nucleic acids can be, for example, analyzed to produce data. The data can be recorded. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some examples, the nucleic acids produced can be sequenced or contacted with markers to produce a genetic profile, a molecular profile, a marker profile, a haplotype, or any combination thereof. In some examples, the genetic profile or nucleotide sequence is recorded on a computer readable medium. In other examples, the methods may further comprise using the nucleic acids produced from plants, plant parts, plant cells or seeds in a plant breeding program, for example in making crosses, selection and/or advancement decisions in a breeding program. Crossing includes any type of plant breeding crossing method, including but not limited to crosses to produce hybrids, outcrossing, selfing, backcrossing, locus conversion, introgression and the like. Favorable genotypes and or marker profiles, optionally associated with a trait of interest, may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes. In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLID from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme, and expression methods. In some examples, no reference genome sequence is needed in order to complete the analysis. Variety R20T2013 and its plant parts can be identified through a molecular marker profile. Such plant parts may be either diploid or haploid. The plant part includes at least one cell of the plant from which it was obtained, such as a diploid cell, a haploid cell or a somatic cell. Also provided are plants and plant parts substantially benefiting from the use of variety R20T2013 in their development, such as variety R20T2013 comprising a locus conversion.

Locus Conversions of Sorghum Line R20T2013

Variety R20T2013 represents a new base genetic line into which a new locus or trait may be introduced. Direct transformation and backcrossing represent two methods that can be used to accomplish such an introgression. The term locus conversion is used to designate the product of such an introgression.

To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Locus conversions can be used to add or modify one or a few traits of such a line such as yield, disease resistance, pest resistance and plant performance in varying or extreme weather conditions.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of R20T2013 may be characterized as having essentially the same phenotypic traits as R20T2013. The traits used for comparison may be those traits shown in Table 1. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A locus conversion of R20T2013 will retain the genetic integrity of R20T2013. For example, a locus conversion of R20T2013 can be developed when DNA sequences are introduced through backcrossing (Hallauer et al., 1988), with a parent of R20T2013 utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, OR, where it is demonstrated that a backcross conversion can be made in as few as two backcrosses. A locus conversion of R20T2013 can be determined through the use of a molecular profile. A locus conversion of R20T2013 would have 92%, 93%, 94%, 95%, 96%, 97%, 98% or 99% of the molecular markers, or molecular profile, of R20T2013. Examples of molecular markers that could be used to determine the molecular profile include Restriction Fragment Length Polymorphisms (RFLP), Polymerase Chain Reaction (PCR) analysis, and Simple Sequence Repeats (SSR), and Single Nucleotide Polymorphisms (SNPs).

Genetic Modification and Transformation of Sorghum Line R20T2013

Transgenes, genetic editing or modification and transformation methods facilitate engineering of the genome of plants to contain and express heterologous genetic elements, such as foreign genetic elements, additional copies of endogenous elements, or modified versions of native or endogenous genetic elements in order to alter at least one trait of a plant in a specific manner. Any sequences, such as DNA, whether from a different species or from the same species, which have been stably inserted into a genome using transformation are referred to herein collectively as "transgenes" and/or "transgenic events". Transgenes can be moved from one genome to another using breeding techniques which may include crossing, backcrossing or double haploid production. In some embodiments, a transformed variant of R20T2013 may comprise at least one transgene or genetic modification but could contain at least 1, 2, 3, 4, 5, 6, 7, 8, 9, 10 transgenes or genetic modifications and no more than 15, 14, 13, 12, 11, 10, 9, 8, 7, 6, 5, 4, 3, or 2 transgenes or genetic modifications. Transformed versions of the claimed sorghum variety R20T2013 containing and inheriting the transgene thereof are provided. F1 hybrid seed of R20T2013 are provided which are produced by crossing varieties 2PWBB63A and 2PWJK39R wherein one or both varieties 2PWBB63A and 2PWJK39R comprise a transgene introduced, for example, by backcrossing or genetic transformation and which transgene is inherited by the F1 hybrid R20T2013 seed.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11 (9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39 (12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1).

Plant transformation methods may involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been engineered into a particular sorghum plant using transformation techniques, could be moved into another line using traditional breeding techniques that are well known in the plant breeding arts. For example, a backcrossing approach could be used to move a transgene from a transformed sorghum plant to an elite inbred line and the resulting progeny would comprise a transgene. Also, if an inbred line was used for the transformation then the transgenic plants could be crossed to a different line in order to produce a transgenic hybrid sorghum plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. For example, see, U.S. Pat. No. 6,118,055.

With transgenic plants according to the present discovery, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) Anal. Biochem. 114:92-96.

A genetic map can be generated, primarily via conventional Restriction Fragment Length Polymorphisms (RFLP), Polymerase Chain Reaction (PCR) analysis, and Simple Sequence Repeats (SSR), and Single Nucleotide Polymorphisms (SNPs), which identifies the approximate chromosomal location of the integrated DNA molecule coding for the foreign protein. For exemplary methodologies in this regard, see, Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNP, and sequencing, all of which are conventional techniques.

Likewise, by means of the present discovery, plants can be genetically engineered to express various phenotypes of agronomic interest. Exemplary transgenes implicated in this regard include, but are not limited to, those categorized below.

1. Genes that create a site for site specific DNA integration.

This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants", *Plant Cell Rep* 21:925-932 and WO 99/25821, which are hereby incorporated by reference. Other systems that may be used include the Gin recombinase of phage Mu (Maeser, et al., 1991), the Pin recombinase of *E. coli* (Enomoto, et al., 1983), and the R/RS system of the pSR1 plasmid (Araki, et al., 1992).

2. Genes that affect abiotic stress resistance (including but not limited to flowering, panicle/glume and seed development, enhancement of nitrogen utilization efficiency, altered nitrogen responsiveness, drought resistance or tolerance, cold resistance or tolerance, and salt resistance or tolerance) and increased yield under stress.

For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521 and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. Nos. 10/817,483 and 09/545,334 where cytokinin expression is modified resulting in plants with increased stress tolerance, such as drought tolerance, and/or increased yield. Also see WO0202776, WO003052063, JP2002281975, U.S. Pat. No. 6,084,153, WO0164898, U.S. Pat. Nos. 6,177,275 and 6,107,547 (enhancement of nitrogen utilization and altered nitrogen responsiveness). For ethylene alteration, see, US Patent Application Publication Numbers 2004/0128719, 2003/0166197 and WO200032761. For plant transcription factors or transcriptional regulators of abiotic stress, see e.g., US Patent Application Publication Number 2004/0098764 or US Patent Application Publication Number 2004/0078852.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), and WO2004076638 and WO2004031349 (transcription factors).

3. Transgenes that confer or contribute to an altered grain characteristic, such as:

A. Altered phosphorus content, for example, by the introduction of a phytase-encoding gene would enhance breakdown of phytate, adding more free phosphate to the transformed plant or by up-regulation of a gene that reduces phytate content. For example, this could be accomplished, by cloning and then re-introducing DNA associated with one or more of the alleles, such as the LPA alleles, identified in mutants characterized by low levels of phytic acid, such as in Raboy, et al. (1990).

B. Altered fatty acids, for example, by down-regulation of stearoyl-ACP desaturase to increase stearic acid content of the plant. See Knultzon, et al., Proc. Natl. Acad. Sci. USA 89:2624 (1992).

C. Altered carbohydrates effected, for example, by altering a gene for an enzyme that affects the branching pattern of starch, a gene altering thioredoxin. (See, U.S. Pat. No. 6,531,648). See, Shiroza, et al., (1988) J. Bacteriol 170:810 (nucleotide sequence of *Streptococcus mutans* fructosyltransferase gene), Steinmetz, et al., (1985) Mol. Gen. Genet. 200:220 (nucleotide sequence of *Bacillus subtilis* levansucrase gene), Pen, et al., (1992) Bio/Technology 10:292 (production of transgenic plants that express *Bacillus licheniformis* alpha-amylase), Elliot, et al., (1993) Plant Molec Biol 21:515 (nucleotide sequences of tomato invertase genes), Søgaard, et al., (1993) J. Biol. Chem. 268:22480 (site-directed mutagenesis of barley alpha-amylase gene) and Fisher, et al., (1993) Plant Physiol 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Altered antioxidant content or composition, such as alteration of tocopherol or tocotrienols. For example, see, U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).

E. Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that confer male sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. A dominant nuclear gene, Ms(tc) controlling male sterility. See, Elkonin, L. A., Theor. Appl. Genet. (2005) 111(7): 1377-1384.

B. A tapetum-specific gene, RTS, a sorghum anther-specific gene is required for male fertility and its promoter sequence directs tissue-specific gene expression in different plant species. Luo, Hong, et al., Plant Molecular Biology., 62(3): 397-408 (12) (2006). Introduction of a deacetylase gene under the control of a tapetum-specific promoter and with the application of the chemical N-Ac-PPT. See International Publication No. WO 01/29237.

C. Introduction of various stamen-specific promoters. Anther-specific promoters which are of particular utility in the production of transgenic male-sterile monocots and plants for restoring their fertility. See, U.S. Pat. No. 5,639,948. See also, International Publication Nos. WO 92/13956 and WO 92/13957.

D. Introduction of the barnase and the barstar genes. See, Paul, et al., Plant Mol. Biol., 19: 611-622 (1992).

For additional examples of nuclear male and female sterility systems and genes, see also, U.S. Pat. Nos. 5,859,341, 6,297,426, 5,478,369, 5,824,524, 5,850,014, and 6,265,640. See also, Hanson, Maureen R., et al., "Interactions of Mitochondrial and Nuclear Genes That Affect Male Gametophyte Development," Plant Cell., 16:S154-S169 (2004), all of which are hereby incorporated by reference.

A. Modification of RNA editing within mitochondrial open reading frames. See, Pring, D. R., et al, Curr. Genet. (1998) 33(6): 429-436; Pring, D. R., et al., J. Hered. (1999) 90(3): 386-393; Pring, D. R., et al., Curr. Genet. (2001) 39(5-6): 371-376; and Hedgcoth, C., et al., Curr. Genet. (2002) 41 (5): 357-365.

B. Cytoplasmic male sterility (CMS) from mutations at atp6 codons. See, Kempken, F., FEBS. Lett. (1998): 441(2): 159-160.

C. Inducing male sterility through heat shock. See, Wang, L., Yi Chuan Xue Bao. (2000) 27(9): 834-838.

D. Inducing male sterility through treatment of streptomycin on sorghum callus cultures. See, Elkonin, L. A., et al., Genetica (2008) 44 (5): 663-673.

5. Transgenes That Confer Tolerance to a Herbicide, For Example:

(A) A herbicide that inhibits the growing point or meristem, such as an imidazolinone or a sulfonylurea. Exemplary genes in this category code for mutant acetolactate synthase (ALS) and acetohydroxyacid synthase (AHAS) enzyme as described, for example, in U.S. Pat. Nos. 5,605,011; 5,013,659; 5,141,870; 5,767,361; 5,731,180; 5,304,732; 4,761,373; 5,331,107; 5,928,937; and 5,378,824; US Patent Publication No. 20070214515, and international publication WO 96/33270.

(B) Glyphosate (tolerance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835, which discloses the nucleotide sequence of a form of EPSPS which can confer glyphosate tolerance. U.S. Pat. No. 5,627,061 also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582.

Glyphosate tolerance is also imparted to plants that express a gene that encodes a glyphosate oxido-reductase enzyme as described more fully in U.S. Pat. Nos. 5,776,760 and 5,463,175. In addition, glyphosate tolerance can be imparted to plants by the over expression of genes encoding glyphosate N-acetyltransferase. See, for example, US2004/0082770; US2005/0246798; and US2008/0234130. A DNA molecule encoding a mutant aroA gene can be obtained under ATCC accession No. 39256, and the nucleotide sequence of the mutant gene is disclosed in U.S. Pat. No. 4,769,061. European Patent Application No. 0 333 033 and U.S. Pat. No. 4,975,374 disclose nucleotide sequences of glutamine synthetase genes which confer tolerance to herbicides such as L-phosphinothricin. The nucleotide sequence of a phosphinothricin-acetyl-transferase gene is provided in European Patent Nos. 0 242 246 and 0 242 236. See also, U.S. Pat. Nos. 5,969,213; 5,489,520; 5,550,318; 5,874,265; 5,919,675; 5,561,236; 5,648,477; 5,646,024; 6,177,616 B1; and 5,879,903. Exemplary genes conferring resistance to phenoxy propionic acids, cyclohexanediones and cyclohexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene) such as bromoxynil. Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Other genes that confer tolerance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) A herbicide that inhibits protoporphyrinogen oxidase (protox or PPO) is necessary for the production of chlorophyll, which is necessary for all plant survival. The protox enzyme serves as the target for a variety of herbicidal compounds. PPO-inbibitor herbicides can inhibit growth of all the different species of plants present, causing their total destruction. The development of plants containing altered protox activity which are tolerant to these herbicides are described, for example, in U.S. Pat. Nos. 6,288,306 B1; 6,282,837 B1; and 5,767,373; and international patent publication WO 01/12825.

(F) Dicamba (3,6-dichloro-2-methoxybenzoic acid) is an organochloride derivative of benzoic acid which functions by increasing plant growth rate such that the plant dies.

6. Transgenes That Confer Resistance to Insects or Disease and That Encode, For Example:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*), McDowell and Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, MD), for example, under ATCC Accession Nos. 40098, 67136, 31995 and 31998. Other non-limiting examples of *Bacillus thuringiensis* transgenes being genetically engineered are given in the following patents and patent applications: 5, 188,960; 5,689,052; 5,880,275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018, 615; 11/404,297; 11/404,638; 11/471,878; 11/780,501; 11/780,511; 11/780,503; 11/953,648; and Ser. No. 11/957, 893.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini and Grossi-de-Sa (2002) Toxicon, 40 (11): 1515-1539; Ussuf et al. (2001) Curr Sci. 80 (7): 847-853; and Vasconcelos and Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monoterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, and U.S. Pat. Nos. 6,563,020; 7,145,060 and 7,087,810.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum.*

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366: 469 (1993), which shows that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995), Pieterse and Van Loon (2004) Curr. Opin. Plant Bio. 7(4): 456-64 and Somssich (2003) Cell 113(7):815-6.

(P) Antifungal genes (Cornelissen and Melchers, PI. Physiol. 101:709-712, (1993) and Parijs et al., Planta 183: 258-264, (1991) and Bushnell et al., Can. J. of Plant Path. 20 (2):137-149 (1998). Also see U.S. application Ser. Nos. 09/950,933; 11/619,645; 11/657,710; 11/748,994; 11/774, 121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716, 820; 5,792,931; 5,798,255; 5,846,812; 6,083,736; 6,538, 177; 6,388,171 and 6,812,380.

(R) Cystatin and cysteine proteinase inhibitors. See U.S. Pat. No. 7,205,453.

(S) Defensin genes. See WO03000863 and U.S. Pat. Nos. 6,911,577; 6,855,865; 6,777,592 and 7,238,781.

(T) Genes conferring resistance to nematodes. See e.g. PCT Application WO96/30517; PCT Application WO93/ 19181, WO 03/033651 and Urwin et al., Planta 204:472-479 (1998), Williamson (1999) Curr Opin Plant Bio. 2 (4): 327-31; and US U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, CA (1995).

(V) Genes that confer resistance to Brown Stem Rot, such as described in U.S. Pat. No. 5,689,035.

(W) Genes that confer resistance to *Colletotrichum*, such as described in US Patent publication US20090035765. This includes the Rcg locus that may be utilized as a single locus conversion.

Seed Treatments and Cleaning

Provided are methods of harvesting the grain of the F1 plant of variety R20T2013 and using the grain, F2, as seed for planting. Also provided are methods of using the seed of variety R20T2013, F1, as seed for planting. Embodiments include cleaning the seed, treating the seed, and/or conditioning the seed. Cleaning the seed includes removing foreign debris such as weed seed, chaff, and non-seed plant matter from the seed. Conditioning the seed can include controlling the temperature and rate of dry down and storing seed in a controlled temperature environment. Seed treatment is the application of a composition to the seed such as a coating or powder. Methods for producing a treated seed include the step of applying a composition to the seed or seed surface. Seeds are provided which have on the surface a composition. Some examples of compositions are insecticides, fungicides, pesticides, antimicrobials, germination inhibitors, germination promoters, cytokinins, and nutrients. Carriers such as polymers can be used to increase binding to the seed.

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C.D.S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Uses of Sorghum

Sorghum is used as livestock feed, as sugar or grain for human consumption, as biomass, and as raw material in industry. Sorghum grain can be used as livestock feed, such as to beef cattle, dairy cattle, hogs and poultry. In some embodiments, the plant is used as livestock feed in the form of fodder, silage, hay and pasture. In some embodiments, commodity plant products produced from hybrid seed such as food, feed, forage, and syrup are provided.

Provided are uses of sorghum in the form of bread, porridge, confectionaries and as an alcoholic beverage. Grain sorghum may be ground into flour and either used directly or blended with wheat or corn flour in the preparation of food products. In addition to direct consumption of the grain, sorghum has long been used in many areas of the world to make beer. The uses of sorghum, in addition to human consumption of kernels, include both products of dry and wet milling industries. The principal products of sorghum dry milling are grits, meal and flour. Starch and other extracts for food use can be provided by the wet milling process.

Also provided are uses of sorghum as an industrial raw material. Industrial uses include sorghum starch from the wet-milling industry and sorghum flour from the dry milling industry. Sorghum starch and flour have application in the paper and textile industries. Other industrial uses include applications in adhesives, building materials and as oil-well muds. Considerable amounts of sorghum, both grain and plant material, can be used in industrial alcohol production.

Characteristics of R20T2013

Hybrid sorghum line R20T2013 was developed by Pioneer Hi-Bred International, Inc. Sorghum line R20T2013 has all, or essentially all, the phenotypic characteristics shown in Table 1. Provided are seed of sorghum line R20T2013, plants of sorghum line R20T2013, plant parts of sorghum line R20T2013, and plant cells of sorghum line R20T2013.

Hybrid sorghum line R20T2013 can be made by crossing inbreds 2PWBB63A and 2PWJK39R. Locus conversions of hybrid sorghum variety R20T2013 can be made by crossing inbreds 2PWBB63A and 2PWJK39R wherein one or both of 2PWBB63A and 2PWJK39R comprise a locus conversion (s). Hybrid sorghum line R20T2013 has shown uniformity and stability within the limits of environmental influence for all, or essentially all, of the phenotypic traits such as described in the Variety Description Information (Table 1).

Hybrid sorghum line R20T2013 can be advantageously used in accordance with the breeding methods described herein and those known in the art to produce other hybrids and progeny plants retaining desired trait combinations of hybrid sorghum line R20T2013. Provided are methods for producing a sorghum plant by crossing a first parent sorghum plant with a second parent sorghum plant wherein either the first or second parent sorghum plant is hybrid sorghum line R20T2013. Further, both first and second parent sorghum plants can come from the hybrid sorghum line R20T2013. Either the first or the second parent plant may be male sterile. Processes for making a plant may comprise crossing sorghum line R20T2013 with another plant.

The terms variants, modification and mutant refer to a hybrid seed or a plant produced by that hybrid seed which is phenotypically similar to R20T2013.

The foregoing discovery has been described in detail by way of illustration and example for purposes of exemplification. However, it will be apparent that changes and modifications such as single gene modifications and mutations, somaclonal variants, variant individuals selected from populations of the plants of the instant variety, and the like, are considered to be within the scope of the present discovery. All references disclosed herein whether to journal, patents, published applications and the like are hereby incorporated in their entirety by reference.

DEPOSITS

Applicant has made a deposit of at least 625 seeds of parental sorghum inbred varieties 2PWBB63A and 2PWJK39R with the Provasoli-Guillard National Center for Marine Algae and Microbiota (NCMA), 60 Bigelow Drive, East Boothbay, ME 04544, USA, with NCMA Accession Numbers 202403027 and 202510053, respectively. The seeds deposited with the NCMA on Mar. 22, 2024 for 202403027 and on Oct. 23, 2025 for 202510053 were obtained from the seed of the variety maintained by Pioneer Hi-Bred International, Inc., 7250 NW 62nd Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon issuance of any claims in the application, the Applicant will make the deposit available to the public pursuant to 37 C.F.R. § 1.808. These deposits of the seed of parental sorghum inbred varieties for Sorghum Variety R20T2013 will be maintained in the NCMA depository, which is a public depository, for a period of 30 years, or 5 years after the most recent request, or for the enforceable life of the patent, whichever is longer, and will be replaced if it becomes nonviable during that period. Additionally, Applicant will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of the rights granted under this patent or rights applicable to Sorghum Variety R20T2013 and/or its parental sorghum inbred varieties 2PWBB63A and 2PWJK39R under either the patent laws or the Plant Variety Protection Act (7 USC 2321 et seq.). Unauthorized seed multiplication is prohibited.

TABLE 1

Variety Descriptions of R20T2013 based on Morphological, Agronomic and Quality Traits

| Trait | Description |
|---|---|
| Kind | Sorghum |
| Use Class: | grain |
| Days from planting to mid-anthesis | 76 |
| Plant Coleoptile | green |
| Plant pigment | purple |
| Plant height in inches | 42 |
| Stalk Height (cm from soil to top of panicle) | 107 |
| Plant: Natural height of foliage at panicle emergence | medium |
| Plant: Total height at maturity | medium |
| Diameter of main stalk | mid stout |
| Waxy Bloom | present |
| Number of Tillers | few |
| Stem Sweetness | insipid |
| Stem Juiciness | dry |
| Panicle Exertion | medium |
| Degree of Senescence | intermediate |
| Leaf Color | dark green |
| Leaf: Width of blade of first leaf below flag leaf | moderate |

TABLE 1-continued

| Variety Descriptions of R20T2013 based on Morphological, Agronomic and Quality Traits | |
|---|---|
| Trait | Description |
| Leaf margin | wavy |
| Leaf attitude or erectness | horizontal |
| Ligule | present |
| Leaf midrib color (first leaf below flag leaf) | intermediate |
| Panicle Anther Color (at flowering) | dark yellow |
| Panicle Length (cm) | 33 |
| Panicle Density | semi-compact |
| Panicle Shape at maturity | oval |
| Length of central rachis (% of panicle length) | 25% |
| Panicle erectness | erect |
| Rachis branches at grain maturity | horizontal |
| Rachis Branch Average | intermediate |
| Panicle Type | More cylindrical sorghum panicle type |
| Glume length at maturity | intermediate |
| Percent of grain covered by the glume | 50% |
| Glume Texture | leathery |
| Glume color at grain maturity | mahogany |
| Glume Hairiness or pubescence | intermediate |
| Glume Venation | absent |
| Glume Transverse Wrinkle | absent |
| Glume Awns | absent |
| Roots | fibrous |
| Grain Testa | absent |
| Grain Mesocarp Thickness | intermediate |
| Grain Epicarp Color (Genetic) | red |
| Grain Spreader (Tannin in Pericarp) | absent |
| Grain Intensifier | absent |
| Grain Color (Appearance) | light red |
| Grain Endosperm Color | yellow |
| Grain Endosperm Type | starchy |
| Grain Endosperm Texture | intermediate |
| Grain Seed Shape | ovate |
| No. of seed per 100 G Genotype | 4997 |

What is claimed is:

1. An F1 hybrid sorghum variety R20T2013 seed produced by crossing a first plant of variety 2PWBB63A with a second plant of variety 2PWJK39R, representative seed of the varieties 2PWBB63A and 2PWJK39R having been deposited under NCMA Accession Numbers 202403027 and 202510053, respectively.

2. The F1 hybrid sorghum variety R20T2013 seed of claim 1, further comprising a seed treatment on the seed.

3. An F1 plant, plant part, or plant cell produced by growing the F1 hybrid sorghum variety R20T2013 seed of claim 1, the plant part comprising at least one cell of sorghum variety R20T2013.

4. The F1 plant, plant part, or plant cell of claim 3, wherein the plant part or plant cell is a pollen or ovule.

5. A method of making a commodity plant product, the method comprising producing the commodity plant product from the plant or plant part of claim 3.

6. A method comprising cleaning the plant part of claim 3, wherein the plant part comprises sorghum grain.

7. A method for producing a second sorghum plant, the method comprising applying plant breeding techniques to the plant or plant part of claim 3 to produce the second sorghum plant.

8. A method comprising:

(a) crossing the plant or plant part of claim 3 with itself or a different plant to produce progeny seed;

(b) growing the progeny seed to produce a progeny plant and crossing the progeny plant with itself or a different plant to produce further progeny seed.

9. A method comprising generating a molecular marker profile from markers bound to nucleic acids isolated from the hybrid sorghum variety R20T2013 plant, plant part, or plant cell of claim 3.

10. A seed of F1 hybrid sorghum variety R20T2013 further comprising a locus conversion, wherein the seed is produced by crossing a first plant of variety 2PWBB63A with a second plant of variety 2PWJK39R; wherein representative seed of the varieties 2PWBB63A and 2PWJK39R have been deposited under NCMA Accession Numbers 202403027 and 202510053, respectively; and wherein at least one of the varieties 2PWBB63A and 2PWJK39R further comprises the locus conversion which is inherited by the seed, and wherein the seed produces a plant which otherwise has all the morphological and physiological characteristics as sorghum variety R20T2013 when grown under the same environmental conditions.

11. The seed of claim 10, further comprising a seed treatment on the seed.

12. The seed of claim 10, wherein the locus conversion confers a property selected from the group consisting of male sterility, site-specific recombination, abiotic stress tolerance, altered phosphate, altered antioxidants, altered fatty acids, altered essential amino acids, altered carbohydrates, herbicide tolerance, insect resistance and disease resistance.

13. A method comprising (a) isolating nucleic acids from the hybrid sorghum variety R20T2013 seed of claim 10; and (b) generating a molecular marker profile from said isolated nucleic acids.

14. An F1 plant, plant part, or plant cell produced by growing the seed of claim 10, wherein the plant part comprises at least one cell of hybrid sorghum variety R20T2013 further comprising a locus conversion.

15. A method comprising cleaning the plant part of claim 14, wherein the plant part comprises sorghum grain.

16. The F1 plant, plant part, or plant cell of claim 14, wherein the plant part or plant cell is a pollen or ovule.

17. A method of making a commodity plant product, the method comprising producing the commodity plant product from the plant or plant part of claim 14.

18. A method for producing a second sorghum plant, the method comprising applying plant breeding techniques to the plant or plant part of claim 14 to produce the second sorghum plant.

19. A method comprising:

(a) crossing the plant or plant part of claim 14 with itself or a different plant to produce progeny seed;

(b) growing the progeny seed to produce a progeny plant and crossing the progeny plant with itself or a different plant to produce further progeny seed.

20. A seed of hybrid sorghum variety R20T2013 further comprising a first single locus conversion, produced by crossing a first plant of variety 2PWBB63A with a second plant of variety 2PWJK39R, wherein representative seed of said varieties 2PWBB63A and 2PWJK39R have been deposited under NCMA Accession numbers 202403027 and 202510053, respectively, and wherein one or both of the first plant and second plant further comprises the single locus conversion, and wherein a plant grown from said seed comprises a trait conferred by said first single locus conversion, and otherwise comprises all the morphological and physiological characteristics as sorghum variety R20T2013 when grown under the same environmental conditions.

* * * * *